United States Patent [19]

Hancock

[11] Patent Number: 5,450,851
[45] Date of Patent: Sep. 19, 1995

[54] ULTRASONIC PROBE ASSEMBLY

[75] Inventor: Joseph D. Hancock, Abington, Pa.

[73] Assignee: Advanced Technology Laboratories, Inc., Bothell, Wash.

[21] Appl. No.: 249,138

[22] Filed: May 25, 1994

[51] Int. Cl.6 .................................................. A61B 8/12
[52] U.S. Cl. ............................ 128/662.06; 128/660.1
[58] Field of Search ............ 128/660.1, 660.03, 662.06; 73/619-621

[56] References Cited

U.S. PATENT DOCUMENTS

| | | | |
|---|---|---|---|
| 4,014,207 | 3/1977 | Meyer et al. | 73/621 |
| 4,149,419 | 4/1979 | Connell, Jr. et al. | 73/621 |
| 4,269,066 | 5/1981 | Fischer | 73/639 |
| 4,272,991 | 6/1981 | Cribbs | 73/621 |
| 4,330,874 | 5/1982 | Sorwick | 367/103 |
| 4,362,058 | 12/1982 | Abele | 73/599 |
| 4,374,525 | 2/1983 | Baba | 128/662.06 |
| 4,375,818 | 3/1983 | Suwaki et al. | 128/662.06 |
| 4,385,521 | 5/1983 | Hagen et al. | 73/619 |
| 4,494,548 | 1/1985 | Buon et al. | 128/660.1 |
| 4,567,895 | 2/1986 | Putzke | 73/639 X |
| 4,637,256 | 1/1987 | Sugiyama et al. | 128/660.09 X |
| 4,732,156 | 3/1988 | Nakamura | 128/660.09 |
| 4,756,313 | 7/1988 | Terwilliger | 128/660.1 |
| 4,757,818 | 7/1988 | Angelsen | 128/660.1 |
| 4,787,247 | 11/1988 | Wuchinich et al. | 73/620 |
| 4,807,634 | 2/1989 | Enjoji et al. | 128/660.01 |
| 4,841,979 | 6/1989 | Dow et al. | 128/660.1 |
| 4,850,362 | 7/1989 | Rello et al. | 128/660.05 |
| 4,913,158 | 4/1990 | Kikuchi et al. | 128/660.1 |
| 5,115,814 | 5/1992 | Griffith et al. | 128/662.06 |
| 5,255,684 | 10/1993 | Rello | 128/662.06 |
| 5,299,578 | 4/1994 | Rotteveel et al. | 128/662.06 |
| 5,307,810 | 11/1994 | Odanaka | 128/662.06 |

FOREIGN PATENT DOCUMENTS 0079525  5/1983  European Pat. Off.
0317049  5/1989  European Pat. Off.

*Primary Examiner*—Francis Jaworski
*Attorney, Agent, or Firm*—W. Brinton Yorks, Jr.

[57] ABSTRACT

An ultrasonic probe assembly in which an ultrasonic transducer is mechanically scanned in response to a drive motor which is located in a housing spaced from the transducer such that the transducer can be positioned in a body cavity of a patient while the housing containing the drive motor remains outside the body of the patient.

16 Claims, 4 Drawing Sheets

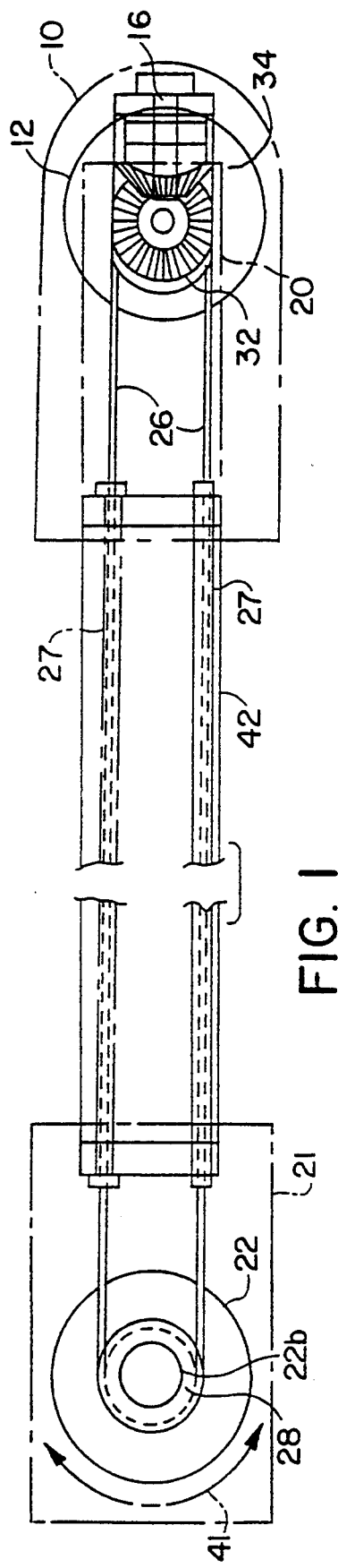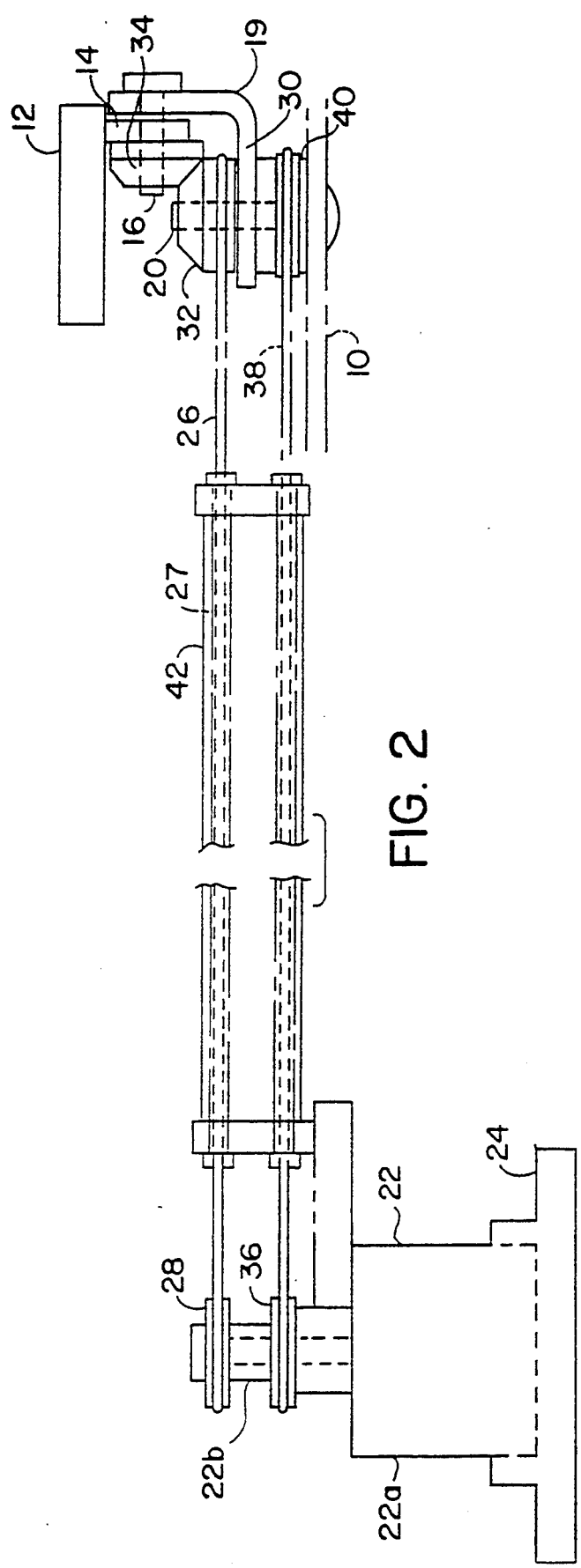

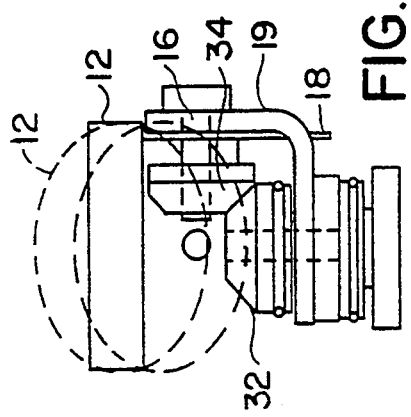
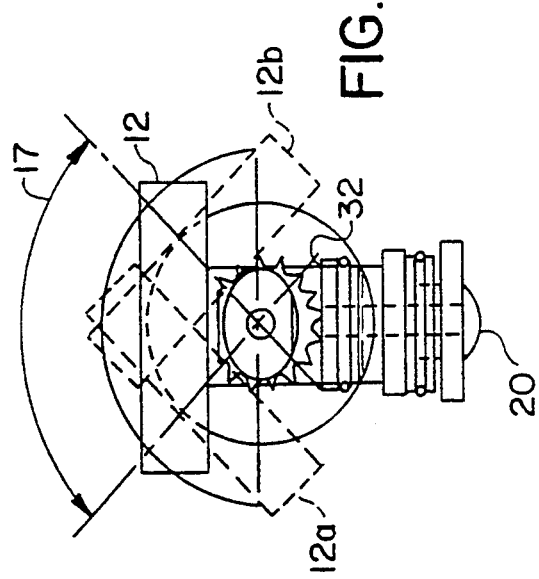
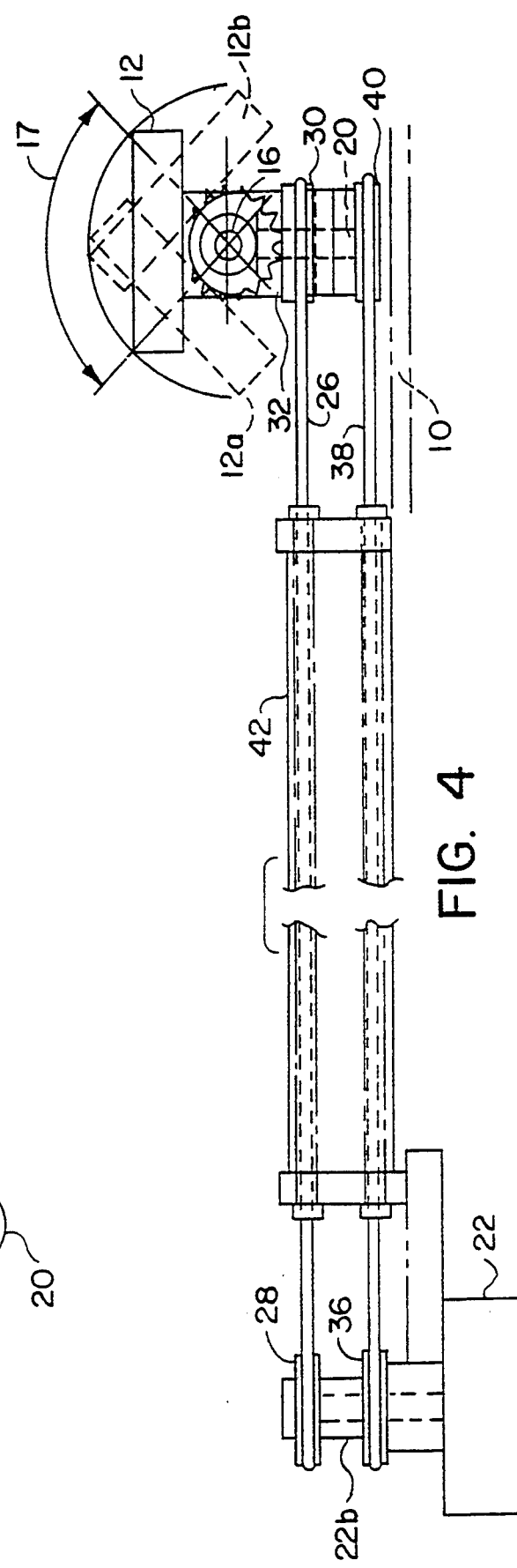

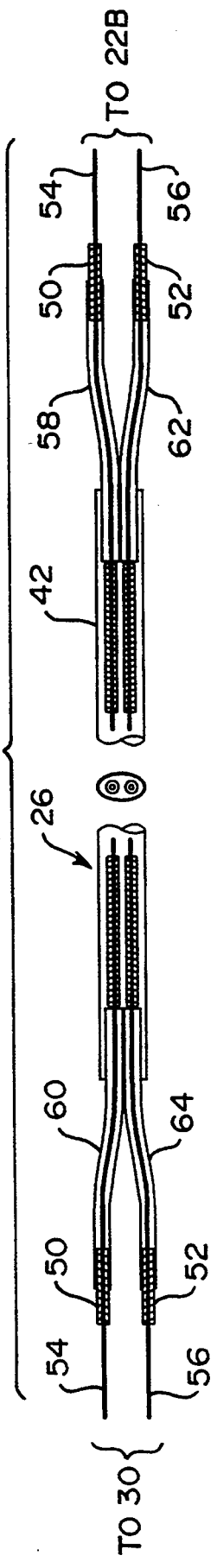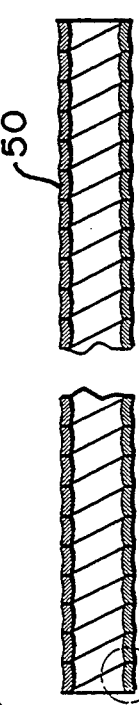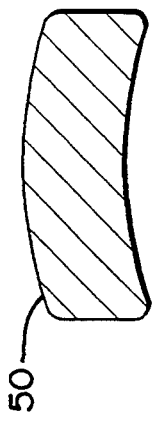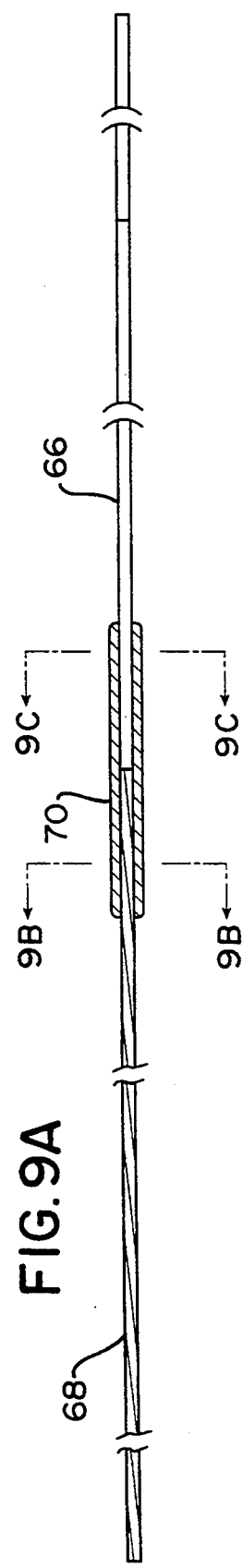

ULTRASONIC PROBE ASSEMBLY

TECHNICAL FIELD

The present invention relates, in general, to ultrasonic imaging and, in particular, to an ultrasonic probe assembly with the ultrasonic transducer arranged for insertion into a body cavity.

BACKGROUND OF THE INVENTION

Ultrasonic probe assemblies having the ultrasonic transducer arranged for insertion into a body cavity (i.e. prostrate probes, esophageal probes, vaginal probes) are in widespread use. Typically, the ultrasonic transducer, the transducer mount mechanism and the motor which imparts scanning movement to the ultrasonic transducer are housed at one end of an endoscope. Power to the motor and electrical signals, from which the image is developed, are conducted along wires extending through the endoscope. In addition, for those ultrasonic probe assemblies arranged for multi-plane scanning, the cables by which the scan plane of the ultrasonic transducer is changed mechanically extend through the endoscope to the transducer mount mechanism from a control remote from the transducer mount mechanism.

It is apparent that the sizes of the ultrasonic transducer, the transducer mount mechanism and the scanning motor dictate the size of the housing inserted into the body cavity. Often, the size of this housing is too large for the desired applications of the ultrasonic probe assembly.

SUMMARY OF THE INVENTION

An ultrasonic probe assembly, constructed in accordance with the present invention, includes a first housing, a ultrasonic transducer and mounting means for mounting the ultrasonic transducer to the first housing for scanning movement of the ultrasonic transducer. Also included in this ultrasonic probe assembly are a second housing spaced from the first housing, a drive motor mounted in the second housing and having an output driver, and coupling means, including flexible connecting means, extending between the output driver of the motor and the ultrasonic transducer for imparting scanning movement to the ultrasonic transducer in response to the output driver. The flexible connecting means have a length which permits positioning the first housing with the ultrasonic transducer within a body cavity of a patient while the second housing remains outside the body of the patient.

When the present invention is incorporated in a multi-plane imaging ultrasonic probe assembly, the assembly also includes second mounting means for mounting the first mounting means and the ultrasonic transducer to the first housing for pivotal movement of the first mounting means about an axis perpendicular to the axis about which the ultrasonic transducer is scanned. Also included are selection means attached to the second housing containing the drive motor for setting a selected pivotal position of the first mounting means and second coupling means, including second flexible connecting means, extending between the selection means and the second mounting means for positioning the first mounting means in response to the selection means. The second flexible connecting means have a length substantially coextensive with the first flexible connecting means.

BRIEF DESCRIPTION OF THE DRAWINGS

FIG. 1 is a top view of one preferred embodiment of an ultrasonic probe assembly constructed in accordance with the present invention.

FIG. 2 is a side view of the FIG. 1 ultrasonic probe assembly.

FIG. 3 is an end view of the FIGS. 1 and 2 ultrasonic probe assembly.

FIG. 4 is a side view of the FIGS. 1 and 2 ultrasonic probe assembly with the ultrasonic transducer positioned to scan in a plane different from its scan plane in FIGS. 1 and 2.

FIG. 5 is an end view of the FIGS. 1 and 2 ultrasonic probe assembly with the ultrasonic transducer positioned to scan as illustrated in FIG. 4.

FIG. 7 illustrates, on an enlarged scale, the coupling means by which scanning movement is imparted to the ultrasonic transducer of the FIGS. 1 through 5 probe assembly.

FIGS. 8A and 8B illustrate, on an enlarged scale, a preferred form of the flexible spring conduit of the FIG. 7 coupling means.

FIGS. 9A, 9B and 9C illustrate, on an enlarged scale, a preferred form of the drive wire of the FIG. 7 coupling means.

DETAILED DESCRIPTION OF THE INVENTION

Figure 6:
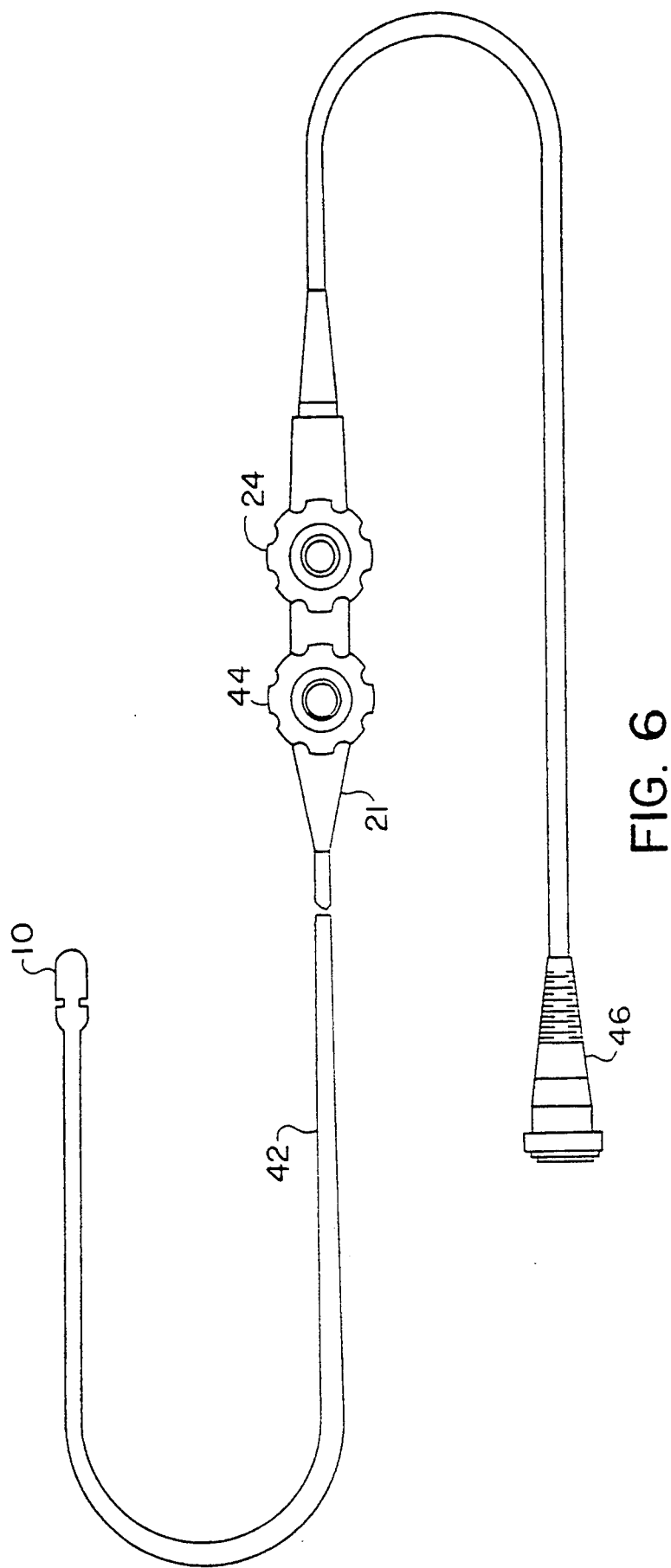
FIG. 6 is a plan view of an endoscope in which the ultrasonic probe assembly of FIGS. 1 through 5 can be incorporated.

Referring to FIGS. 1 through 5, an ultrasonic probe assembly, constructed in accordance with the present invention, includes a first housing 10, an ultrasonic transducer 12, and first mounting means for mounting ultrasonic transducer 12 for scanning movement of ultrasonic transducer 12 about a first axis. Ultrasonic transducer 12 can be of conventional construction and operation such as a 3.5–5 MHz transducer supplied by Echo Ultrasound and used typically for cardiac imaging. Ultrasonic transducer 12 is attached to a leg 14 and is mounted, for the embodiment of the present invention being described, by a pivot shaft 16 on which leg 14 is mounted and which defines an axis for scanning movement of ultrasonic transducer 12. FIG. 3 shows by dashed lines 12a and 12b the range of oscillatory scanning motion of ultrasonic transducer 12. A double-ended arrow 17 defines this range of motion which typically is 100 degrees.

For an application of the present invention in a multi-plane probe assembly, the first mounting means and ultrasonic transducer 12 are mounted to housing 10 for pivotal movement of the first mounting means about a second axis which is perpendicular to the scan axis of transducer 12. This is accomplished by second mounting means which, for the embodiment of the present invention being described, include a bracket 19 and a pivot shaft 20. By this arrangement the plane of scanning of ultrasonic transducer 12 can be changed so that the body such as the heart, which is being imaged can be viewed in different ways (i.e. in longitudinal and transverse sections or any section in between). FIGS. 4 and 5 show ultrasonic transducer 12 positioned to scan in a plane different from the scan plane position of ultrasonic transducer 12 in FIGS. 1, 2 and 3.

An ultrasonic probe assembly, constructed in accordance with the present invention, also includes a second housing 21 spaced from first housing 10 and a drive motor 22 mounted in housing 21 and having a motor housing 22a and an output driver shaft 22b. Drive motor 22, which can be a DC reciprocating motor, provides the drive for oscillatory scanning movement of ultrasonic transducer 12. Drive motor 22 is rotatably mounted in housing 21, so that it can pivot when the scan plane of ultrasonic transducer 12 is to be changed.

Attached to motor housing 22a are selection means, in the form of a knob 24, for setting a selected pivotal position of the first mounting means in housing 10. The position of knob 24 and, therefore, the position of motor 22 determine the scan plane of ultrasonic transducer 12.

An ultrasonic probe assembly, constructed in accordance with the present invention, further includes first coupling means for imparting scanning movement to transducer 12 in response to oscillatory movement of output driver shaft 22b. The first coupling means include, for the embodiment of the present invention described, a flexible connection 26 attached at a first end to a drive pulley 28 which is fixed to output driver shaft 22b of motor 22. Flexible connection 26 also is attached at a second end to a pulley 30 which is mounted on pivot shaft 20 for reciprocating movement. Integral with pulley 30 is a first bevel gear 32 which meshes with a second bevel gear 34 to which leg 14 is attached. As a result, the oscillatory drive provided by motor 22 is imparted to ultrasonic transducer 12 through drive pulley 28, flexible connection 26, pulley 30, bevel gears 32 and 34, and leg 14. The length of flexible connection 26 permits positioning first housing 10 and ultrasonic transducer 12 within a body cavity of a patient while second housing 21 with motor 22 remains outside the body of the patient.

An ultrasonic probe assembly, constructed in accordance with the present invention, further includes second coupling means extending between the scan-plane selection means at housing 21 and the second mounting means at housing 10 for positioning the first mounting means at housing 10 in response to movement of the selection means. The second coupling means include, for the embodiment of the present invention being described, a pulley 36 fixed to motor housing 22a and a second flexible connection 38 fixed at one end to pulley 36 and at a second end to a pulley 40 which is integral with bracket 19. As a result, as knob 24 is turned, as represented by the double-ended arrow 41, this movement is imparted to bracket 19 through motor housing 22a, pulley 36, flexible connection 38 and pulley 40 to change scan plane of ultrasonic transducer 12. The range of scan-plane variation can be up to one hundred eighty degrees. The length of flexible connection 38 is substantially coextensive with flexible connection 26, so that knob 24 with housing 21 is outside the body of the patient while housing 10 and ultrasonic transducer 12 are within a body cavity of the patient.

Preferably, flexible connections 26 and 38 extend through a flexible plastic tube 42. In addition, wires (not shown) which power ultrasonic transducer 12 and conduct imaging signals from transducer 12 extend through flexible plastic tube 42.

FIG. 6 illustrates the ultrasonic probe assembly of FIGS. 1 through 5 incorporated in an endoscope. Knob 24 on housing 21 functions, as previously described, to change the scan plane of the ultrasonic transducer in housing 10. The drive motor (not shown in FIG. 6) is located in housing 21. A second knob 44 on housing 21 controls bending of the end of the flexible endoscope upward, downward and sideways to permit the end of the endoscope to make turns as it is passed through the body to the body cavity at which imaging is to take place. The wires (not shown) which power the ultrasonic transducer (not shown in FIG. 6) and conduct imaging signals from the transducer extend to a connector 46 which is adapted for connection into suitable signal processing and imaging equipment.

Referring to FIG. 7, flexible connection 26 of FIGS. 1 through 5 includes a first flexible spring conduit 50 extending between first housing 10 and second housing 21, a second flexible spring conduit 52 extending between first housing 10 and second housing 21, a first drive wire 54 extending through first flexible spring conduit 50 between output driver 22b of drive motor 22 and pulley 30 of ultrasonic transducer 12, and a second drive wire 56 extending through second flexible spring conduit 52 between output driver 22b of drive motor 22 and pulley 30 of ultrasonic transducer 12. First and second drive wires 54 and 56, after each has been wrapped halfway around pulley 30 from opposite sides, are attached to pulley 30 at diametrically opposite points on the pulley. Each of the flexible spring conduits 50 and 52 is attached at one end to housing 21 and preloaded against housing 10 at its opposite end. As the two lengths of first and second drive wires 54 and 56 to either side of pulley 30 are pulled or pushed in response to the reciprocating movement of output driver shaft. 22b of motor 22, pulley 30 turns.

Flexible connection 26 further includes a first flexible plastic tube 58 fixed to and extending from first housing 10 and through which first flexible spring conduit 50 and first drive wire 54 extend, a second flexible plastic tube 60 fixed to and extending from second housing 21 and through which first flexible spring conduit 50 and first drive wire 54 extend, a third flexible plastic tube 62 fixed to and extending from first housing 10 and through which second flexible spring conduit 52 and second drive wire 36 extend, a fourth flexible plastic tube 64 fixed to and extending from second housing 21 and through which second flexible spring conduit 32 and second drive wire 36 extend. First flexible spring conduit 50, first drive wire 54, second flexible spring conduit 52 and second drive wire 56 extend through flexible plastic tube 42. A first end of flexible plastic tube 42 is attached to first flexible plastic tube 58 and third flexible plastic tube 62 and a second end of flexible plastic tube 42 is attached to second flexible plastic tube 60 and fourth flexible plastic tube 64.

FIGS. 8A and 8B show flexible spring conduits 50 and 52 on an enlarged scale. These parts, commonly known as Bowden conduits, are tightly wrapped helically and are both rigid to provide support columns for the push/pull movement of the drive wires and flexible to permit bending as the ultrasonic transducer and its housing are introduced into a body cavity. The generally rectangular cross-section provides added bearing from one turn to the next resulting in added rigidity when compared to flexible spring conduits having circular cross-sections. In addition, to the extent that the drive wire contacts the inside surface of the flexible spring conduit, the contact is a point contact because of the curved inside surface of the flexible spring conduit.

The arrangement of flexible connection 26 which has just been described results in a connection having reduced hysteresis and backlash. First and second drive wires 54 and 56 are sufficiently flexible to conform to the tight radii of pulley 30 in housing 10 and pulley 28 in housing 21 yet provide sufficient stiffness and rigidity for both push and pull operation.

In addition, with the arrangement of flexible connection 26 which has just been described, nonlubricating acoustic fluid in housing 10 can flow into and through the flexible connection to housing 21 without a detrimental effect on the scanning operation. This avoids the need for a dynamic seal which can accommodate the high-speed push/pull movements of drive wires 54 and 56. As an alternative, however, a dynamic seal can be provided in housing 10, in which case acoustic fluid would not flow into flexible connection 26.

In order to provide increased flexibility of drive wires 54 and 56 about pulley 30 in housing 10, the drive wires preferably are, as shown by FIGS. 9A, 9B and 9B, composed of a relatively long length solid wire portion 66 and a relatively short length multi-strand portion 68 adapted to engage pulley 30 of ultrasonic transducer 12. Solid wire portion 66 and multi-strand portion 68 are attached by suitable means, such as a coupling 70, for example hypodermic tubing. Other means, for example butt-brazing, are possible for attaching these two parts of the drive wires. A similar arrangement can be provided at the opposite ends of the drive wires which are attached to and engage pulley 28 in housing 21.

Flexible connection 38, by which the scan plane of ultrasonic transducer 12 is changed, can be arranged similar to flexible connection 26 just described.

The foregoing has set forth an exemplary and preferred embodiment of the present invention. It will be understood, however, that various other alternative embodiments will occur to those of ordinary skill in the art without departure from the spirit and scope of the present invention.

What is claimed:

1. An ultrasonic probe assembly comprising:
   a first housing;
   an ultrasonic transducer;
   mounting means for mounting said ultrasonic transducer to said first housing for scanning movement of said ultrasonic transducer in a scan plane;
   a second housing spaced from said first housing;
   a drive motor mounted in said second housing; and
   coupling means for imparting scanning movement to said ultrasonic transducer in response to said drive motor, said coupling means having a length which permits positioning said first housing and said ultrasonic transducer within a body cavity of a patient while said second housing remains outside the body of the patient and including:
   (a) a flexible spring conduit extending between said first housing and said second housing,
   (b) a drive wire extending through said flexible spring conduit between said drive motor and said ultrasonic transducer,
      wherein said flexible spring conduit is generally rectangular in cross-section.

2. An ultrasonic probe assembly according to claim 1 wherein said rectangular cross-section flexible spring conduit comprises a winding of wire which is generally rectangular in cross-section and curved in an arc, wherein the convex side of said curved wire faces the interior of said conduit.

3. An ultrasonic probe assembly comprising:
   a first housing;
   an ultrasonic transducer;
   mounting means for mounting said ultrasonic transducer to said first housing for scanning movement of said ultrasonic transducer in a scan plane;
   a second housing spaced from said first housing;
   a drive motor mounted in said second housing and having an output driver; and
   coupling means for imparting scanning movement to said ultrasonic transducer in response to said output driver, said coupling means having a length which permits positioning said first housing and said ultrasonic transducer within a body cavity of a patient while said second housing remains outside the body of the patient and including:
   (a) a first flexible spring conduit extending between said first housing and said second housing,
   (b) a second flexible spring conduit extending between said first housing and said second housing,
   (c) a first drive wire extending through said first flexible spring conduit between said output driver of said drive motor and said ultrasonic transducer, and
   (d) a second drive wire extending through said second flexible spring conduit between said output driver of said drive motor and said ultrasonic transducer;
   wherein said coupling means further include:
   (a) a first flexible plastic tube extending from said first housing and through which said first flexible spring conduit and said first drive wire extend,
   (b) a second flexible plastic tube extending from said second housing and through which said first flexible spring conduit and said first drive wire extend,
   (c) a third flexible plastic tube extending from said first housing and through which said second flexible spring conduit and said second drive wire extend,
   (d) a fourth flexible plastic tube extending from said second housing and through which said second flexible spring conduit and said second drive wire extend, and
   (e) a fifth flexible plastic tube through which first flexible spring conduit, said first drive wire, said second flexible spring conduit and said second drive wire extend and having:
      (1) a first end to which said first flexible plastic tube and said third flexible plastic tube are attached, and
      (2) a second end to which said second flexible plastic tube and said fourth flexible plastic tube are attached.

4. An ultrasonic probe assembly according to claim 3 wherein the cross-section of each of said first flexible spring conduit and said second flexible spring conduit is generally rectangular.

5. An ultrasonic probe assembly according to claim 3 wherein each of said first drive wire and said second drive wire has a relatively long length solid wire portion, a relatively short length multi-strand portion attached to said ultrasonic transducer, and means for attaching said solid wire portion and said multi-strand portion.

6. An ultrasonic probe assembly according to claim 3 wherein each of said first drive wire and said second drive wire has a relatively long length solid wire portion, a first relatively short length multi-strand portion attached to said ultrasonic transducer, a second relatively short length multi-strand portion attached to said output driver of said drive motor, and means for attaching said multi-strand portions to opposite ends of said solid wire portion.

7. An ultrasonic probe assembly comprising:
a first housing;
an ultrasonic transducer;
first mounting means for mounting said ultrasonic transducer for scanning movement of said ultrasonic transducer in a selected scan plane about a first axis;
second mounting means for mounting said first mounting means and said ultrasonic transducer to said first housing for pivotal movement of said first mounting means with respect to said first housing about a second axis which is perpendicular to said first axis;
a second housing spaced from said first housing;
a drive motor mounted in said second housing and having an output driver;
selection means attached to said motor housing for setting a selected pivotal position of said first mounting means corresponding to said selected scan plane;
first coupling means for imparting scanning movement to said ultrasonic transducer in response to said output driver, said coupling means having a length which permits positioning said first housing and said ultrasonic transducer within a body cavity of a patient while said second housing remains outside the body of the patient and including:
(a) a first flexible spring conduit extending between said first housing and said second housing,
(b) a second flexible spring conduit extending between said first housing and said second housing,
(c) a first drive wire extending through said first flexible spring conduit between said output driver of said drive motor and said ultrasonic transducer, and
(d) A second drive wire extending through said second flexible spring conduit between said output driver of said drive motor and said ultrasonic transducer; and
second coupling means extending between said selection mean and said second mounting means for positioning said first mounting means in response to movement of said selection means, said second coupling means having a length substantially coextensive with said first coupling means;
wherein said first coupling means further include:
(a) a first flexible plastic tube extending from said first housing and through which said first flexible spring conduit and said first drive wire extend,
(b) a second flexible plastic tube extending from said second housing and through which said first flexible spring conduit and said first drive wire extend,
(c) a third flexible plastic tube extending from said first housing and through which said second flexible spring conduit and said second drive wire extend,
(d) a fourth flexible plastic tube extending from said second housing and through which said second flexible spring conduit and said second drive wire extend, and
(e) a fifth flexible plastic tube through which said first flexible spring conduit, said first drive wire, said second flexible spring conduit and said second drive wire extend and having:

(1) a first end to which said first flexible plastic tube and said third plastic are attached, and
(2) a first end to which said second flexible plastic tube and said fourth flexible plastic are attached.

8. An ultrasonic probe assembly according to claim 7 wherein the cross-section of each of said first flexible spring conduit and said second flexible spring conduit is generally rectangular.

9. An ultrasonic probe assembly according to claim 7 wherein each of said first drive wire and said second drive wire has a relatively long length solid wire portion, a relatively short length multi-strand portion attached to said ultrasonic transducer, and means for attaching said solid wire portion and said multi-strand portion.

10. An ultrasonicprobe assembly according to claim 7 wherein each of said first drive wire and said second drive wire has a relatively long length solid wire portion, a first relatively short length multi-strand portion attached to said ultrasonic transducer, a second relatively short length multi-strand portion attached to said output driver of said drive motor, and means for attaching said multi-strand portions to opposite ends of said solid wire portion.

11. An ultrasonic probe assembly comprising:
a first housing;
an ultrasonic transducer;
mounting means for mounting said ultrasonic transducer to said first housing for movement of said ultrasonic transducer to scan a selected scan plane;
a second housing spaced from said first housing and including means for controlling the movement of said ultrasonic transducer;
coupling means extending between said controlling means and said mounting means for positioning said ultrasonic transducer in response to said controlling means, said coupling means having a length which permits positioning said first housing and said ultrasonic transducer within a body cavity of a patient while said second housing remains outside the body of the patient and including:
(a) a flexible spring conduit extending between said first housing and said second housing,
(b) a drive wire extending through said flexible spring conduit between said controlling means and said ultrasonic transducer,
wherein said flexible spring conduit comprises a winding of wire which is generally rectangular in cross-section and curved in an arc so that said cross-section has a convex side and a concave side, wherein said convex side of said curved wire faces the interior of said conduit.

12. An ultrasonic probe assembly according to claim 11 wherein the cross-section of said flexible spring conduit is generally rectangular.

13. An ultrasonic probe assembly comprising:
a first housing;
an ultrasonic transducer;
mounting means for mounting said ultrasonic transducer to said first housing for movement of said ultrasonic transducer to a selected scan plane;
a second housing spaced from said first housing;
selection means attached to said second housing for setting a selected pivotal position of said mounting means corresponding to said selected scan plane;
coupling means extending between said selection means and said mounting means for positioning said ultrasonic transducer in response to movement of said selection means, said coupling means having a length which permits positioning said first housing and said ultrasonic transducer within a body cavity of a patient while said second housing remains outside the body of the patient and including:

(a) a first flexible spring conduit extending between said first housing and said second housing, (b) a second flexible spring conduit extending between said first housing and said second housing, (c) a first drive wire extending through said first flexible spring conduit between said selection means and said ultrasonic transducer, and (d) a second drive wire extending through said second flexible spring conduit between said selection means and said ultrasonic transducer;

wherein said coupling means further include:

(a) a first flexible plastic tube extending from said first housing and through which said first flexible spring conduit and said first drive wire extend, (b) a second flexible plastic tube extending from said second housing and through which said first flexible spring conduit and said first drive wire extend, (c) a third flexible plastic tube extending from said first housing and through which said second flexible spring conduit and said second drive wire extend, (d) a fourth flexible plastic tube extending from said second housing and through which said second flexible spring conduit and said second drive wire extend, and (e) a fifth flexible plastic tube through which first flexible spring conduit, said first drive wire, said second flexible spring conduit and said second drive wire extend and having:

(1) a first end to which said first flexible plastic tube and said third flexible plastic are attached, and (2) a first end to which said second flexible plastic tube and said fourth flexible plastic are attached.

14. An ultrasonicprobe assembly according to claim 13 wherein the cross-section of each of said first flexible spring conduit and said second flexible spring conduit is generally rectangular.

15. An ultrasonic probe assembly according to claim 13 wherein each of said first drive wire and said second drive wire has a relatively long length solid wire portion, a relatively short length multi-strand portion attached to said ultrasonic transducer, and means for attaching said solid wire portion and said multi-strand portion.

16. An ultrasonic probe assembly according to claim 13 wherein each of said first drive wire and said second drive wire has a relatively long length solid wire portion, a first relatively short length multi-strand portion attached to said ultrasonic transducer, a second relatively short length multi-strand portion attached to said selection means, and means for attaching said multi-strand portions to opposite ends of said solid wire portion.

* * * * *